United States Patent
Shifflette (10) Patent No.: US 8,079,948 B2
(45) Date of Patent: Dec. 20, 2011

(54) ARTICLE COMPRISING AN IMPELLER

(75) Inventor: J. Michael Shifflette, Alachua, FL (US)

(73) Assignee: NuCardia, Inc., El Dorado Hills, CA (US)

( * ) Notice: Subject to any disclaimer, the term of this patent is extended or adjusted under 35 U.S.C. 154(b) by 707 days.

(21) Appl. No.: 12/201,561

(22) Filed: Aug. 29, 2008

(65) Prior Publication Data

US 2009/0062597 A1    Mar. 5, 2009

Related U.S. Application Data (60) Provisional application No. 60/968,864, filed on Aug. 29, 2007.

(51) Int. Cl.
*A61M 1/10* (2006.01)
(52) U.S. Cl. ................. 600/16; 417/423.1
(58) Field of Classification Search ............ 417/420, 417/423.1; 600/16, 17
See application file for complete search history.

(56) References Cited

U.S. PATENT DOCUMENTS

| | | |
|---|---|---|
| 3,510,229 A | 5/1970 | Smith |
| 4,625,712 A | 12/1986 | Wampler |
| 4,753,221 A | 6/1988 | Kensey |
| 4,817,586 A | 4/1989 | Wampler |
| 4,846,152 A | 7/1989 | Wampler et al. |
| 4,919,647 A | 4/1990 | Nash |
| 4,969,865 A | 11/1990 | Hwang |
| 5,092,844 A | 3/1992 | Schwartz et al. |
| 5,112,292 A | 5/1992 | Hwang et al. |
| 5,169,378 A | 12/1992 | Figuera |
| 5,376,114 A | 12/1994 | Jarvik |
| 5,405,383 A | 4/1995 | Barr |
| 5,588,812 A | 12/1996 | Taylor et al. |
| 5,749,855 A * | 5/1998 | Reitan ............ 604/151 |
| 5,755,784 A | 5/1998 | Jarvik |
| 5,776,190 A | 7/1998 | Jarvik |
| 5,888,241 A | 3/1999 | Jarvik |
| 6,007,478 A | 12/1999 | Siess et al. |
| 6,058,593 A | 5/2000 | Siess |
| 6,139,487 A | 10/2000 | Siess |
| 6,176,822 B1 | 1/2001 | Nix et al. |
| 6,176,848 B1 | 1/2001 | Ran et al. |
| 6,200,260 B1 | 3/2001 | Bolling |
| 6,227,820 B1 | 5/2001 | Jarvik |
| 6,245,007 B1 | 6/2001 | Bedingham et al. |
| 6,299,575 B1 | 10/2001 | Bolling |

(Continued)

FOREIGN PATENT DOCUMENTS

WO    9639956 A1    12/1996

(Continued)

OTHER PUBLICATIONS

Ingelbrecht, Peter, "PCT Application No. PCT/US2008/075993 Search Report", Feb. 19, 2009, Publisher: EPO.

*Primary Examiner* — Carl H Layno
*Assistant Examiner* — Frances Oropeza
(74) *Attorney, Agent, or Firm* — DeMont & Breyer, LLC (57) ABSTRACT

An impeller for use in conjunction with a percutaneously-insertable blood pump or other rotatable equipment includes a blade that is segmented into a plurality of overlapping or abutting bladelets. In some embodiments, the bladelets are foldable and one side of each bladelet is concave.

30 Claims, 8 Drawing Sheets

U.S. PATENT DOCUMENTS

| | | |
|---|---|---|
| 6,387,037 B1 | 5/2002 | Bolling et al. |
| 6,406,422 B1 | 6/2002 | Landesberg |
| 6,428,464 B1 | 8/2002 | Bolling |
| 6,497,698 B1 | 12/2002 | Fonger et al. |
| 6,508,787 B2 | 1/2003 | Erbel et al. |
| 6,527,699 B1 | 3/2003 | Goldowsky |
| 6,533,716 B1 | 3/2003 | Schmitz-Rode et al. |
| 6,544,216 B1 | 4/2003 | Sammler et al. |
| 6,620,004 B1 | 9/2003 | Piper |
| 6,623,475 B1 | 9/2003 | Siess |
| 6,644,125 B1 | 11/2003 | Siess et al. |
| 6,685,621 B2 | 2/2004 | Bolling et al. |
| 6,716,157 B2 | 4/2004 | Goldowsky |
| 6,719,720 B1 | 4/2004 | Voelker et al. |
| 6,790,171 B1 | 9/2004 | Grundeman et al. |
| 6,794,789 B2 | 9/2004 | Siess et al. |
| 6,808,483 B1 | 10/2004 | Ortiz et al. |
| 6,889,082 B2 | 5/2005 | Bolling et al. |
| 6,942,611 B2 | 9/2005 | Siess |
| 7,011,620 B1 | 3/2006 | Siess |
| 7,022,100 B1 | 4/2006 | Aboul-Hosn et al. |
| 7,070,555 B2 | 7/2006 | Siess |
| 7,258,679 B2 | 8/2007 | Moore et al. |
| 7,371,210 B2 | 5/2008 | Brock et al. |
| 7,393,181 B2 | 7/2008 | McBride et al. |
| 2003/0105383 A1 | 6/2003 | Barbut et al. |
| 2003/0163019 A1 | 8/2003 | Goldowsky |
| 2004/0241019 A1 | 12/2004 | Goldowsky |
| 2005/0049696 A1 | 3/2005 | Siess |
| 2006/0008349 A1 | 1/2006 | Khaw |
| 2006/0062672 A1 | 3/2006 | McBride et al. |
| 2008/0103591 A1 | 5/2008 | Siess |
| 2008/0114339 A1 * | 5/2008 | McBride et al. ........... 604/891.1 |

FOREIGN PATENT DOCUMENTS

| | | |
|---|---|---|
| WO | 0121249 A1 | 3/2001 |
| WO | 0139817 A2 | 6/2001 |
| WO | 0174419 A1 | 10/2001 |
| WO | 0241935 | 5/2002 |
| WO | 0243791 A1 | 6/2002 |
| WO | 0245775 A2 | 6/2002 |

* cited by examiner

ARTICLE COMPRISING AN IMPELLER

STATEMENT OF RELATED CASES

This case claims priority of U.S. patent application Ser. No. 60/968,864 filed Aug. 29, 2007, which is incorporated herein by reference.

BACKGROUND

An impeller is a rotating component that includes a hub and at least one blade. In operation, the impeller is used to accelerate and/or pressurize a fluid. More particularly, an impeller converts the rotary mechanical energy of a drive (e.g., a motor, etc.) into kinetic energy (flow) and potential energy (pressure) of a fluid being acted upon. Impellers are used in various types of equipment, including pumps, water jets, agitated tanks, washing machines, and vacuum cleaners, to name but a few.

The impeller is designed to enable a pump, etc., to achieve certain performance characteristics, such as a certain mass flow rate, pressure ratio, and/or efficiency. Device performance is ultimately a function of the operating conditions (e.g., inlet pressure, temperature, fluid density, etc.) as well as geometrical parameters of the impeller (e.g., hub diameter, blade geometry, etc.).

Impeller blades often have a very complex blade geometry intended to optimize hydrodynamic efficiency or meet other design criteria. Furthermore, the structure of impeller blades can vary dramatically as a function of intended application. Consider, for example, an airplane propeller blade or mixer blade. These blades tend to be relatively long in span and short in chord length. Contrast those blades with a screw-type impeller blade (e.g., Archimedes screw, etc.) having a single helical vane that exhibits a significant degree of wrap around the central hub. These screw-type blades are relatively short in span and long in chord length.

There are some specialized applications in which the impellers might have additional design requirements, such as an ability to expand and collapse. One such application is the percutaneously-inserted blood pump.

A blood pump is a cardiac-assist device that is useful as an intervention for some patients who have acute heart failure or who are at risk of developing it. An effective cardiac assist device assumes some of the heart's pumping function, thereby unloading the heart and enabling it to recover. The blood pump is typically intended as a temporary measure, usually in operation for less than a week.

Percutaneously-inserted blood pumps are designed to be inserted into a patient using a minimally-invasive procedure. These blood pumps are usually inserted via established cath-lab techniques, such as by inserting the blood pump into a peripheral vessel (e.g., femoral artery, etc.) and advancing it to the ascending aorta or the heart (e.g., Seldinger, etc.). To be percutaneously inserted into a peripheral vessel, a blood pump must be quite small. In particular, it is desirable for these blood pumps to have a 12-French (4 millimeter) or smaller catheter. This places a severe constraint on the size of the impeller blades and, hence, the amount of blood that the device can pump.

In an attempt to address this size constraint, the "expandable" blood pump has been proposed. This type of pump, which is suitably small for percutaneous insertion, includes an impeller that expands once in place within the heart or larger vasculature nearby. The blade span attained by the expanded impeller is greater than is otherwise possible for a non-expandable impeller (that is also percutaneously inserted). As a consequence, the expandable impeller can pump more blood per revolution and operate at a lower rotational speed. Most expandable blood pumps use one of several different implementations of the expandable impeller: inflatable impellers, pivoting impellers, or foldable impellers. Some examples of prior-art blood pumps that use these types of impellers are discussed below.

U.S. Pat. No. 6,981,942 discloses a percutaneously-insertable blood pump having an inflatable housing and an inflatable impeller, which includes an inflatable hub and a single blade-row of inflatable blades. The housing is attached to a long sheath that couples the pump (ultimately sited in/near the heart) to extracorporeal elements, such as a motor and source of pressurized air. A drive shaft that couples the impeller to the motor and inflation tubes for inflating the housing and impeller are disposed in the sheath.

U.S. Pat. No. 5,749,855 discloses a percutaneously-insertable blood pump having a pivoting impeller. The impeller comprises a single blade row of two blades that are surrounded by an expandable cage. A drive cable extends from an extracorporeal motor to the distal end of the cage. In the absence of an applied, axially-directed force, the cage and impeller remain in a collapsed state.

The drive cable is designed so that its inner part is movable relative to its outer part. As the inner part of the drive cable is drawn in the proximal direction by an axially-applied force (e.g., by a medical practitioner tugging on the inner part), relative movement between the inner and outer parts of the drive cable expands the cage and pivots the blades into a deployed state. The deployed propeller can then freely spin within the expanded cage.

U.S. Pat. No. 6,533,716 discloses a percutaneously-insertable blood pump having a foldable helical rotor. The rotor consists of a helical frame, which is embodied as a helically-twisted segment of Nitinol wire. Both ends of the helically-twisted segment are coupled to an elastic band that lies along the axis of rotation of the helical frame. A surface of the rotor "blade" is formed from a membrane that extends between the helical frame and the centrally-disposed elastic band. The membrane is formed from a spongy, woven tissue.

The helical rotor is in a collapsed state for insertion into the vascular system. In this state, a tube overlies the helical frame and forces it into an elongated configuration along the central axis. The centrally-disposed elastic band is under maximum tension and the covering membrane is compressed. When the covering tube is withdrawn, the elongated Nitinol wire contracts axially and assumes the helical shape. As this occurs, the elastic band contracts and the membrane forms a smooth surface that functions as the surface of the rotor.

U.S. Pat. No. 4,753,221 discloses a percutaneously-insertable blood pump that includes attributes of both inflatable and foldable impellers. This blood pump comprises a catheter, the distal end of which is formed from a flexible material that is capable of expanding. Blades, which are disposed in a single blade row, are formed from an elastic material and are disposed in the catheter at the flexible region. When the catheter is in a delivery or collapsed state, the blades are "bent over," substantially parallel to the rotational axis of the pump. To deploy the blades, the distal end of the catheter is enlarged by inflating a balloon that couples to the exterior of the catheter. As the distal end of the catheter expands, the blades unfold into an operational position wherein they extend orthogonally to the rotational axis.

U.S. Pat. No. 4,919,647 discloses a percutaneously-insertable blood pump having a catheter to which four foldable impeller blades arranged in a single blade row are coupled. The blades are formed of an elastic material and are biased to naturally project radially outward. The blades are disposed in the distal end of a catheter, which has a cup-shaped form and is made from an expandable material. For insertion into a patient, the impeller blades and the cup-shaped portion are contracted radially inward, such as by placing the catheter within a tubular guide. When the guide is removed, the blades and the cup-shaped portion expand.

U.S. Publ. Pat. Appl. No. 2008/0114339 discloses a percutaneously-insertable blood pump having an impeller with foldable blades arranged in a plurality of blade rows. This reference discloses that it is difficult to fold a long helical blade that exhibits a substantial amount of wrap around the central hub. To address this problem, the reference discloses that a long blade should be segregated into two, three or perhaps more shorter blades that are arranged (i.e., spaced apart) into a like number of blade rows.

Although impeller design is a well-understood discipline, the expandable impeller, especially in the context of a blood pump, raises a variety of design challenges. In particular, and among any other issues, careful consideration must be paid to the structural adaption of the impeller that enables it to expand/collapse and the manner in which expansion/collapse is actuated. These issues are important because they typically affect the structural configuration of the surrounding pump structure (e.g., pump housing, etc.) and the way in which the impeller is integrated in the surrounding structure.

It is notable that even though the patent literature is replete with expandable blood pumps, including those discussed above, not one of them is currently in use. A need therefore remains for an expandable impeller that can be used in percutaneously-insertable blood pumps, among other applications.

SUMMARY

The present invention provides an impeller useful in pumps and other rotating equipment. In the illustrative embodiment, the impeller is used in conjunction with a percutaneously-inserted, expandable, cardiac-assist device.

In approaching the problem of developing an impeller suitable for use in a percutanteously-insertable blood pump, the present inventor recognized that it would be desirable for the impeller to operate at relatively lower speeds (e.g., less than about 5,000 rpm). Operating at relatively lower speeds will extend the life of a drive cable that couples an extracorporeal motor to the pump. To pump the typically-desired amount of blood (i.e., about 2.5 liters per minute or more) when operating at such lower speeds requires an impeller having a blade span that is too large to introduce through the human vasculature via a percutaneous technique. As a consequence, the present inventor reached the conclusion that a collapsible/expandable impeller design was indicated.

Typically, impeller design and blade geometry is dictated almost exclusively by hydrodynamic considerations. That is why impeller blades usually have an airfoil or other highly complex shape. Once a particular geometry is developed, materials of construction and blade thickness are selected to provide the requisite strength, etc. And that is one reason why such blades are usually relatively thicker near the root and thinner near the tip.

The present inventor, however, approached the task of impeller design from a different perspective. In particular, the impetus for the impeller design and blade geometry was based primarily on considerations of structural rigidity and strength. That is, since the impeller blades, at least in some embodiments, are intended to be foldable, they must be able to resist inadvertent buckling or folding during operation.

Impeller blades typically have a pair of opposed faces: a pressure face that induces relative motion of the fluid as the blade rotates and a suction face that induces motion of the fluid via suction. The pressure and suction faces are usually curved in the same general direction, defining an airfoil shape. Some embodiments of impellers disclosed herein do not exhibit this airfoil geometry.

Analogizing to a metallic wind-up tape measure, the present inventor recognized that a blade having a pressure face that was concave and a suction face that was convex would provide excellent resistance to folding when the force was applied to the concave face. So, in accordance with the present invention, the structural rigidity of the impeller blades is imparted through blade geometry whereas in the prior art, it is primarily imparted through materials selection.

Consider the metallic tape measure. It can be extended horizontally many feet against gravity, yet remain substantially straight, if the tape is in a concave-side-up orientation. If, however, the tape measure is inverted, so that it assumes a concave-side-down orientation, the tape will readily succumb to gravity by folding. The tape measure therefore buckles readily if force is applied to the convex side, but is far more effective at resisting buckling if the force is applied to the concave side. In other words, the curvature of the tape measure provides rigidity against buckling/folding when exposed to loads, but only in one direction.

This configurationally-imparted rigidity is very advantageous for an expandable impeller. Given a required rigidity and a particular material of construction, an impeller having the concave/convex geometry described herein can be formed from less material than would otherwise be possible with conventional designs. Less torque is therefore required to drive the impeller to given speed. This places less stress on the drive cable, which has historically been a point of weakness for percutaneously-insertable blood pumps.

Furthermore, the property of one-way rigidity can be very advantageous for an expandable impeller. In particular, in applications that permit, the impeller can be collapsed for extraction by simply reversing the direction of rotation of the impeller.

The use of a concave profile for the pressure face of an impeller blade was the first of several important insights. To gain the benefit of this geometry, the present inventor recognized that it would be important to have a relatively small radius of curvature (i.e., a relatively sharp curve) at the root of the blade to resist folding. If the radius of curvature were to flatten towards infinite curvature (i.e., a straight line) at the root, the ability to resist folding would decrease. Yet, from the perspective of pumping fluid, a much greater radius of curvature (i.e., flatter curve) is desirable near the tip of the blade, since this provides better flow tangency (to the blade), which provides for more efficient pumping.

The aforementioned criteria dictate a blade that is very narrow in chord length near the root but quite wide in chord length at the tip. Notwithstanding the sharply curved root and its potential benefit for rigidity, it is likely that the moment created at the blade tip during operation would collapse a blade having such an extreme tip-to-root aspect ratio.

The present inventor recognized that these countervailing requirements could be reconciled by segmenting the blade into a plurality of discrete "bladelets." Neighboring bladelets are spaced apart at the root but, as a minimum, abut each other at the tip. Preferably, neighboring bladelets will actually overlap each other beginning at some radial distance short of the tip. Segmenting a blade in this manner permits a small radius of curvature at the root of a bladelet and a substantially greater radius of curvature at the tip without resulting in an extreme tip-to-root aspect ratio as with a "full" non-segmented blade. Yet, a "blending" of adjacent bladelets occurs to provide a substantially continuous helical blade, particularly at greater radial distances from the hub where most of the pumping work is accomplished. This maintains the efficiency of the impellers disclosed herein.

Rigidity notwithstanding, impellers described herein must be appropriately efficient and any design thereof must be vetted using computational fluid dynamics, as is known to those skilled in the art.

For example, in some embodiments, there will be open space between adjacent bladelets beneath the tips thereof. Fluid (e.g., blood, etc.) will pass through this space, thereby resulting in decreased impeller efficiency. To prevent that from happening, in some embodiments, a membrane is disposed over or between the bladelets.

In some embodiments, an impeller for use in conjunction with a percutaneously-insertable blood pump will therefore advantageously include a blade that is segmented into a plurality of overlapping or abutting bladelets, wherein the bladelets are foldable, wherein one side of each bladelet is concave and the other side is convex, and wherein the root of each bladelet is smaller in chord length and has a smaller radius of curvature than the tip thereof. Furthermore, the bladelets are covered by a membrane. The impellers described herein are axial-flow impellers. In some other embodiments, impellers in accordance with the present teachings are implemented as mixed-flow impellers (both axial and radial flow).

Impellers possessing some but not all of the features described above will have utility and provide benefits in a variety of applications. Therefore, in some other embodiments, such as may be used for a percutaneously-insertable blood pump or other rotating equipment, an impeller in accordance with the present teachings will include one or more, but not necessarily all, of the following features:
  one or more blades that are segmented into a plurality of overlapping/abutting bladelets; and/or
  a membrane covers the blade(s); and/or
  bladelets in which the pressure face is concave; and/or
  bladelets in which the suction face is convex; and/or
  foldable bladelets; and/or
  the chord length of the root of a bladelet is smaller than the chord length of the tip of the bladelet; and/or
  the radius of curvature of the root of a bladelet is smaller than the radius of curvature of the tip of the bladelet.

By way of example, but not limitation, alternative contemplated impeller designs in accordance with the present teachings include impellers having:
  One or more blades that are segmented into a plurality of overlapping/abutting bladelets that are not foldable and do not have a pressure face that is concave.
  One or more blades that are segmented into a plurality of overlapping/abutting bladelets that are foldable and do not have a pressure face that is concave.
  One or more blades that are segmented into a plurality of overlapping/abutting bladelets that are not foldable and do have a pressure face that is concave.
  A single blade that is foldable and has a pressure face that is concave.

In accordance with the illustrative embodiment, a percutaneously-inserted cardiac-assist device includes a pump assembly that includes an impeller as described herein. The pump assembly is deployed in the aorta, heart, or other major vessels. A drive cable couples the pump assembly to an extracorporeal motor. The motor, via the drive cable, drives the impeller.

DETAILED DESCRIPTION

The following explicit definitions are provided for various terms that appear in this disclosure and the appended claims and are to be used for the interpretation thereof.

"Bladelet" means a discrete segment of an impeller blade; that is, a plurality of bladelets compose a single impeller blade. Tips of adjacent bladelets abut one another or overlap. (Non-traditional definition.)

"Blade row" is a grouping of impeller blades that have a similar axial position along a hub and are typically equally circumferentially spaced apart. By way of example, FIGS. 1A and 1B depict conventional impellers with blades arranged in blade rows.

Figure 1A:
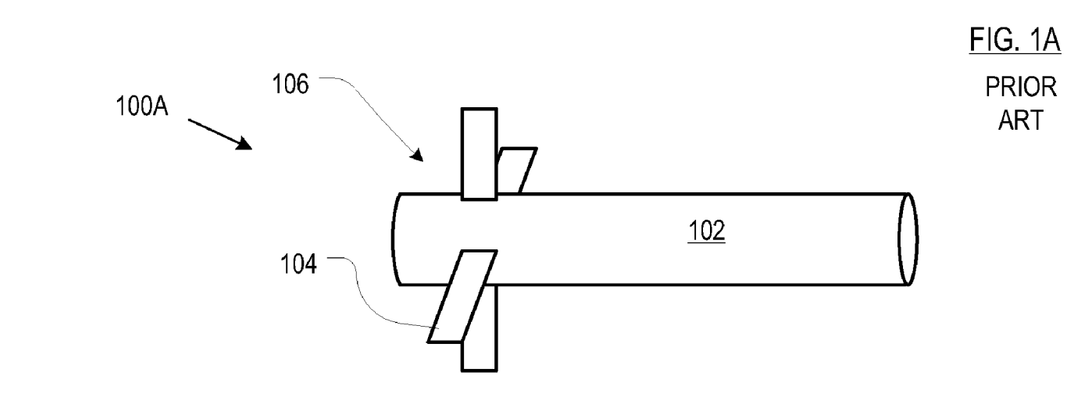
FIG. 1A depicts a representation of a prior-art impeller having a single blade row.
Figure 1B:
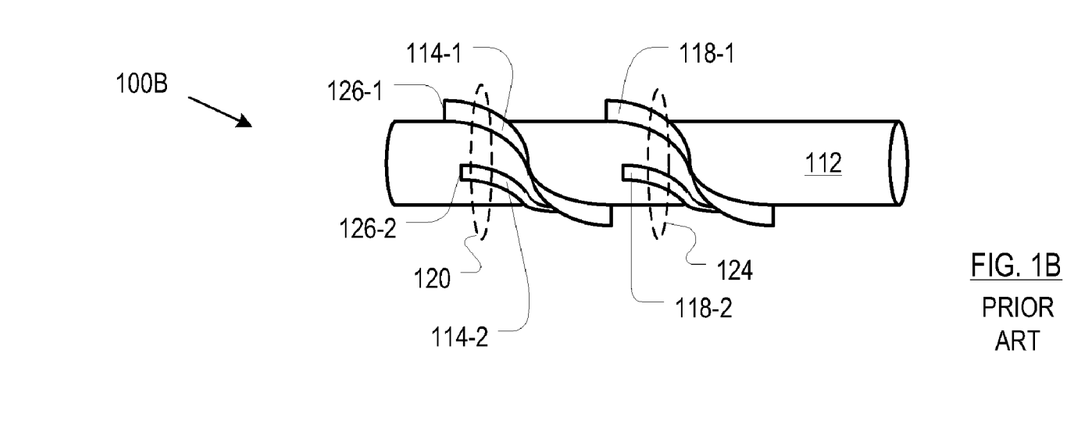
FIG. 1B depicts a representation of a prior-art impeller having two blade rows.

FIG. 1A depicts impeller 100A, which has four blades 104 that are grouped into a single blade row 106 on hub 102. Blades 104 are relatively long in span and short in chord, like those of an airplane propeller. FIG. 1B depicts impeller 100B having hub 112 that supports two blades rows 120 and 124 each having two impeller blades. Blades 114-1 and 114-2 are arranged in blade row 120. Similarly, blades 118-1 and 118-2 are arranged in blade row 124. The blades in blade rows 120 and 124 are long helical blades that exhibit a significant degree of wrap around hub 112.

The blades within a given blade row can exhibit a slight axial offset with respect to each other. For example, in blade row 120 of impeller 100B, leading edge 126-1 of blade 114-1 is forward of leading edge 126-2 of blade 114-2.

"Chord" or ("chord length") is a straight line (or the length thereof) connecting the leading and trailing edges of a blade or bladelet.

"Helix" or "helical" means the curve formed by a straight (or curved) line drawn on a plane when that plane is wrapped around a cylindrical (or conical) surface of any kind, especially a right circular cylinder, as the curve of a (variable-pitch) screw.

"Multi-stage Pump" means a pump having an impeller having blade rows of rotating blades that are interspersed between blade rows of stator (non-rotating) blades that are attached to a housing. As a result, the flow path proceeds from rotor to stator (i.e., from one stage to the next) changing direction and using its momentum from the multiple changes in velocity and direction to achieve higher pressure head.

"Pressure face" means, in the context of an impeller blade or bladelet, the pump-discharge-side face.

"Root" means, in the context of an impeller blade or bladelet, the portion thereof nearest to the hub.

"Suction face" means, in the context of an impeller blade or bladelet, the pump-inlet-side face.

"Tip" means, in the context of an impeller blade or bladelet, the portion furthest from the hub.

Definitions of other terms may appear elsewhere in this disclosure.

Figure 2A:
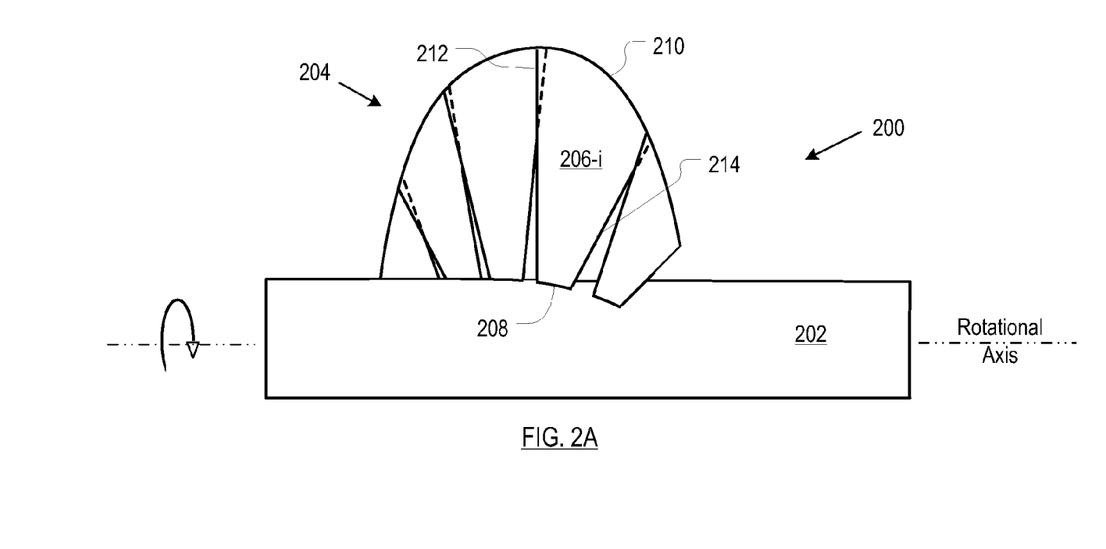
FIG. 2A depicts an embodiment of an impeller comprising bladelets in accordance with the illustrative embodiment of the present invention. The impeller is shown in a deployed or unfolded state and depicts overlap between adjacent bladelets.

FIG. 2A depicts impeller 200 in accordance with the illustrative embodiment of the present invention. Impeller 200 has hub 202 that supports blade 204. Embodiments of an impeller in accordance with the present teachings will usually, but not necessarily, include at least two blades. This is particularly important for impellers that are intended to rotate at speeds of thousands of rpm, such as is required for a percutaneously-inserted blood pump. Impeller 200 can be assumed to possess a second blade, which is not shown for the sake of clarity.

Blade 204 comprises a plurality of bladelets 206-$i$. In this embodiment, blade 204 includes five bladelets. In other embodiments, however, fewer bladelets or more bladelets may suitably be used as a function, for example, of the chord length of blade. More particularly, a blade having a relatively longer chord length will generally have more bladelets than a blade having a relatively shorter chord length.

Each bladelet 206-$i$ is characterized as having root 208, tip 210, leading edge periphery 212 and trailing edge periphery 214. The distance between root 208 and tip 210 depicts the span of the bladelet. The distance between leading edge periphery 212 and trailing edge periphery 214 depicts the extent of bladelet 206-$i$ in the chord-wise direction.

The ratio of the chord of tip 210 to the chord of root 208 of each bladelet is typically in a range from about 1 to about 4, and more typically in a range from about 1.5 to about 3. The ratio of the span of a bladelet to the chord length of tip 210 of a bladelet is typically in a range from about 1 to about 4, and more typically in a range from about 2 to about 4. The ratio of the span of bladelet 206-$i$ to the diameter of hub 202 is typically in a range from about 0.5 to about 3, and more typically in a range from about 1 to about 2.

In the embodiment depicted in FIG. 2A, adjacent bladelets overlap near tip 210. The precise amount of overlap will vary as a function of bladelet geometry; in particular the ratio of the chord length of tip 210 to the chord length of root 208, among other parameters. The greater the ratio, the greater the overlap, as a function of the root spacing between adjacent bladelets.

In some embodiments, overlap is minimal, such that the trailing edge and leading edge at tip 210 of adjacent bladelets simply abut each other. But in all embodiments in accordance with the present teachings, there must be at least minimal contact at the tip of adjacent bladelets. This ensures that the bladelets collectively define a single blade. If space is present between adjacent bladelets, then those bladelets are part of two different blades in two different blade rows.

Figure 2B:
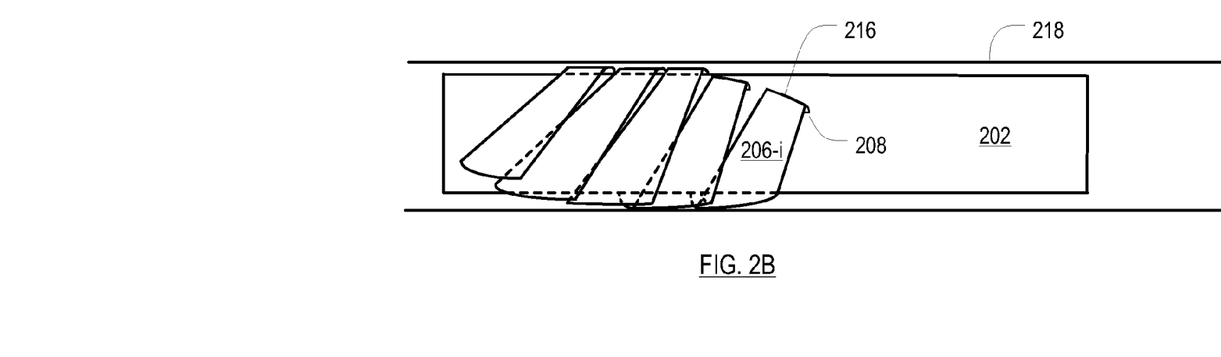
FIG. 2B depicts the impeller of FIG. 2A, but in a folded or delivery state.

In some embodiments, bladelets 206-$i$ are foldable. In such embodiments, FIG. 2A can be considered to depict the bladelets in an unfolded or deployed state and FIG. 2B shows the bladelets in a folded or delivery state. As depicted in FIG. 2B, bladelets 206-$i$ fold at location 216 near root 208.

It is to be understood that, for drawing convenience, Figures that show an impeller in two different states (i.e., unfolded and folded), such as FIGS. 2A/2B (see also FIGS. 5 and 7), do not necessarily depict the same impeller. That is, for pedagogical purposes or other reasons, an impeller might appear as a "right-handed" screw in one Figure and as a "left-handed" screw in what appears to be a complementary Figure. This apparent "inconsistency" is inconsequential since it is not germane to the purpose of the illustrations and will not cause any confusion for those skilled in the art.

In some embodiments, the bladelets are formed from a material that is characterized by a resilience or an ability to return to a specific configuration once a restraining force that is deforming the bladelets is withdrawn. For example, the bladelets can be folded by advancing conduit 218 (e.g., catheter, etc.) over hub 202 and the bladelets. In this folded state, the collapsed diameter of impeller 200 is not substantially larger than the diameter of hub 202.

When conduit 218 is withdrawn, the bladelets unfold (via the potential energy stored in the bladelets during the folding process). Bladelets having an ability to fold and unfold are particularly useful in conjunction with percutaneously-inserted blood pumps. An embodiment of blood pump utilizing an impeller in accordance with the present teachings is described later in this disclosure.

Foldable bladelets can suitably be formed from superelastic Nitinol, stainless steel, or various polymers, such as polyimide, polypropylene, and the like. Hub 202 is suitably formed from stainless steel, nitinol, or any of a variety of polymers.

Figure 3:
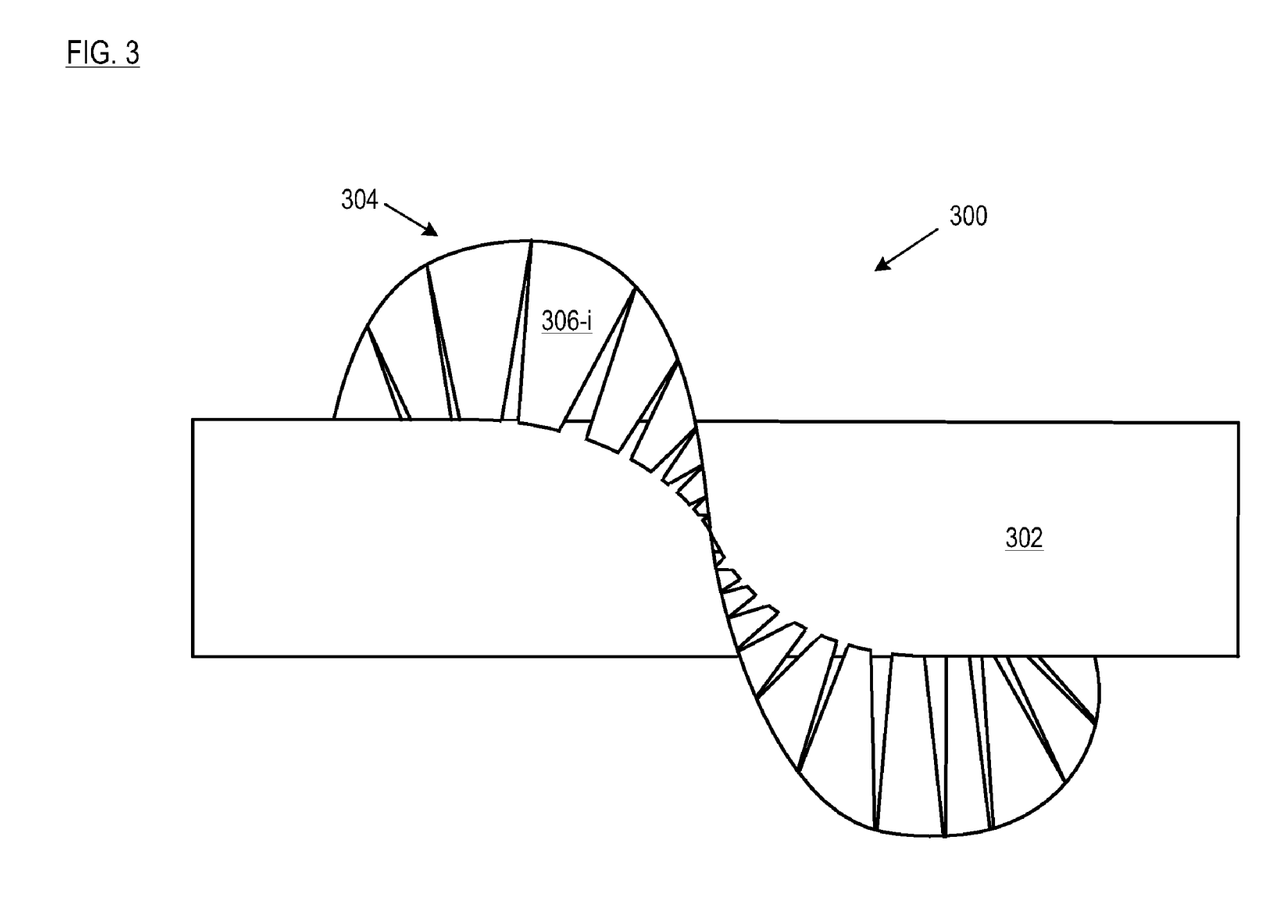
FIG. 3 depicts an embodiment of an impeller comprising abutting bladelets in accordance with the present teachings. The impeller depicts a helical blade that exhibits more than 180 degrees of wrap around the hub.

The geometry (e.g., chord, etc.) of blade 204 is application specific. For most applications, blade 204 will wrap at least partially around hub 202 along a helical path. For use in an expandable blood pump, blade 204 will wrap around hub 202 over an angle that is typically in the range of about 30 to 90 degrees. But, as a function of application specifics, blade 204 can wrap a full 360 degrees or more. FIG. 3 depicts impeller 300, wherein blade 304 comprising a plurality of bladelets 306-$i$ wraps over 180 degrees about hub 302.

As noted in the definition of "blade row," most impellers, and particularly those intended to operate at high rotational speeds, will typically have at least two blades that are equally circumferentially spaced-apart about the impeller hub. That is, the impeller (or blade row) will exhibit n-fold symmetry such that the blades are positioned about 360/n degrees apart from each other about the circumference of the hub, wherein n is the total number of blades in the blade row.

Figures 4A, 4B:
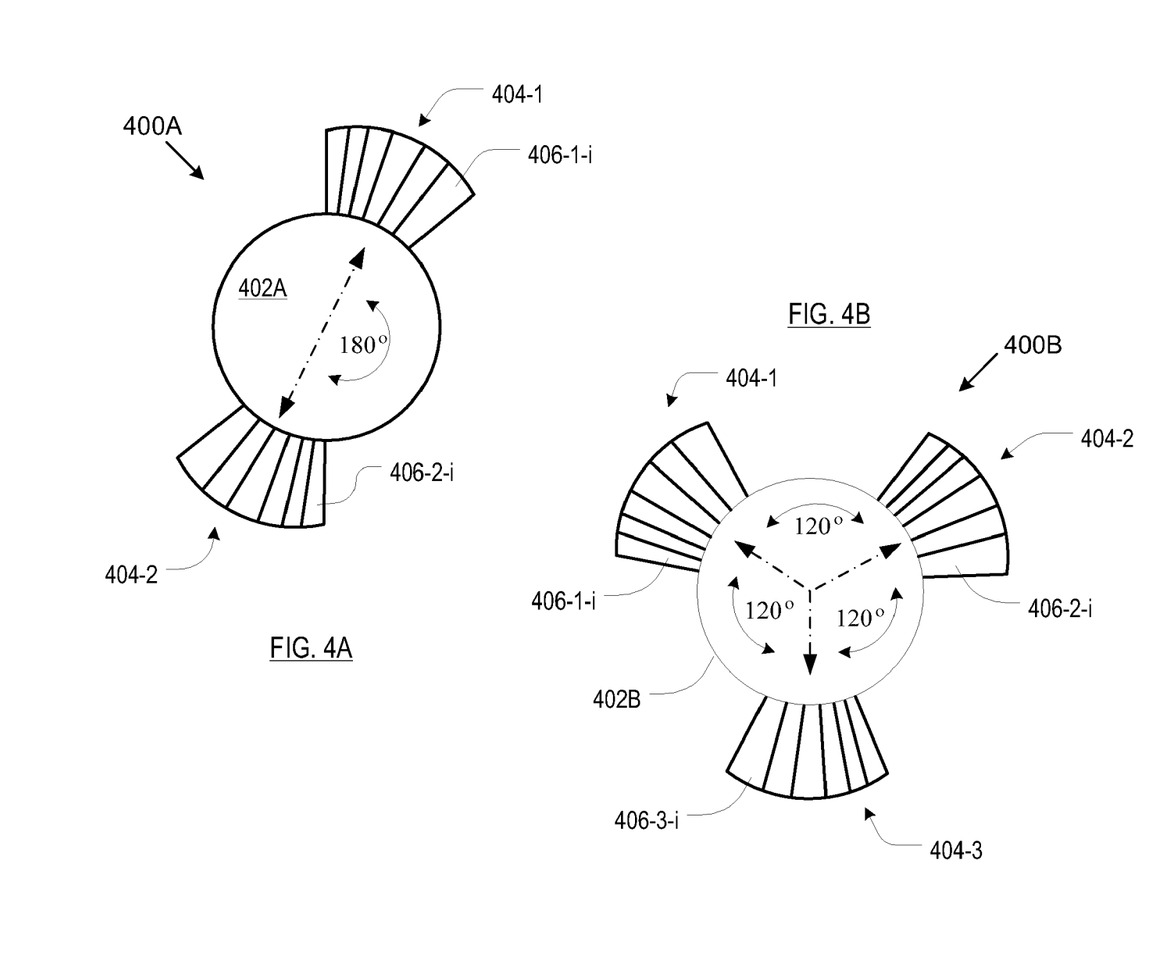
FIG. 4A depicts an end view of an impeller in accordance with the present teachings, wherein the impeller has one blade row with two blades and exhibits bilateral symmetry.
FIG. 4B depicts an end view of an impeller in accordance with the present teachings, wherein the impeller has one blade row with three blades and exhibits tri-lateral symmetry.

FIGS. 4A and 4B depict two examples of impellers in accordance with the present teachings that display n-fold symmetry. FIG. 4A depicts an end view of impeller 400A having two blades 404-1 and 404-2, each comprising a plurality of bladelets 406-1-$i$ and 406-2-$i$, respectively. Blades 404-1 and 404-2 are spaced 360/n degrees apart, where n equals 2, or 180 degrees apart about hub 402A. FIG. 4B depicts an end view of impeller 400B having three blades 404-1, 404-2, and 404-3, each comprising a plurality of bladelets 406-1-$i$, 406-2-$i$, and 406-3-$i$, respectively. Blades 404-1, 404-2, and 404-3 are disposed 360/n degrees apart, where n equals 3, or 120 degrees apart about hub 402B.

Figures 5, 6, 7:
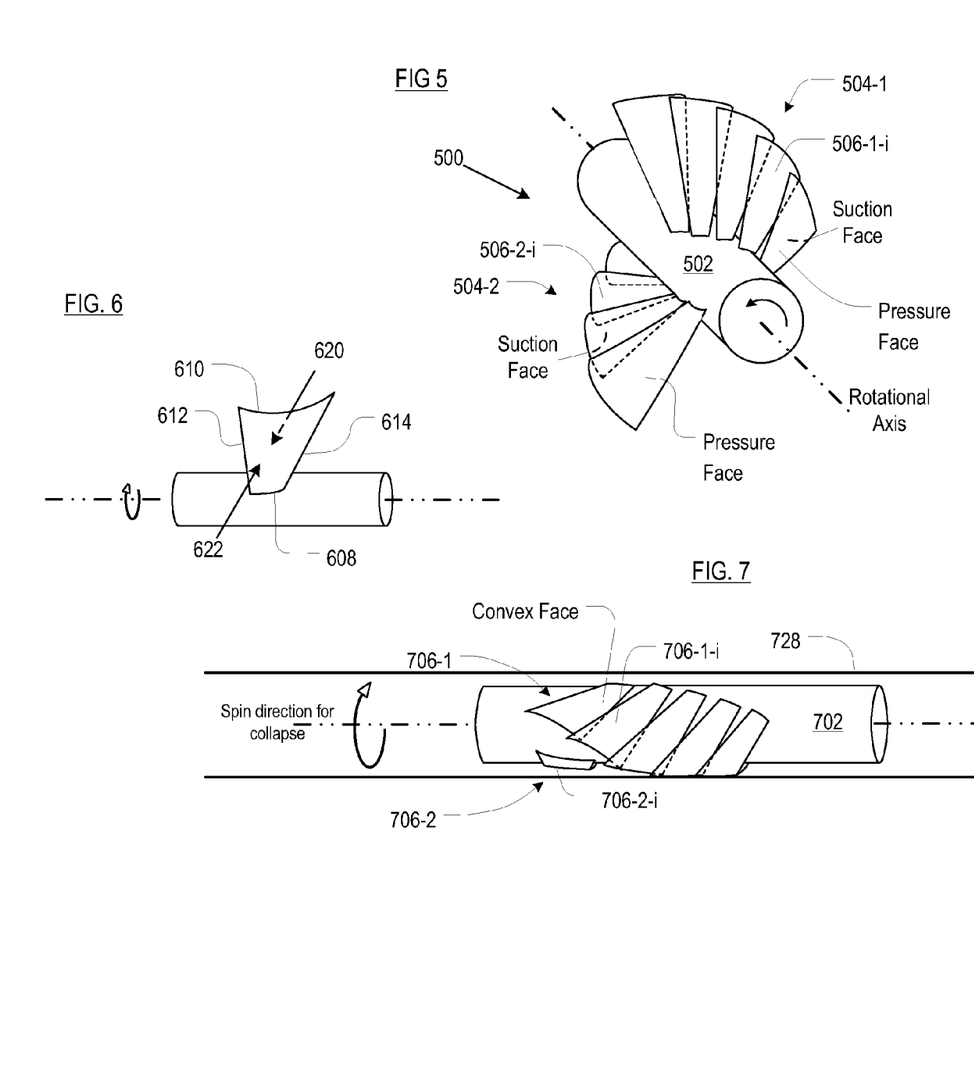
FIG. 5 depicts an embodiment of an impeller comprising bladelets in accordance with the illustrative embodiment of the present invention. The bladelets exhibit a "tape-measure" geometry, wherein one side of each bladelet is concave and the other is convex.
FIG. 6 depicts further detail of a bladelet exhibiting tape-measure geometry in accordance with present teachings.
FIG. 7 depicts an embodiment of an impeller similar to FIG. 5 and wherein the bladelets of the blade are in a folded or delivery state.

FIG. 5 depicts impeller 500 in accordance with a variation of the illustrative embodiment. Impeller 500 includes two blades 504-1 and 504-2 that are organized into a single blade row about hub 502. In accordance with the present teachings, blade 504-1 comprises a plurality of overlapping bladelets 506-1-$i$ and blade 504-2 comprises a plurality of overlapping bladelets 506-2-$i$. In this embodiment, each blade comprises five bladelets.

The operational rotational direction of impeller 500 is indicated by the arrow in FIG. 5 (i.e., counterclockwise). The fluid to be pumped is flowing "out of the page." As a consequence, the pressure face of each bladelet 506-1-$i$ in blade 504-1 is the "visible" face (in FIG. 5). The suction face of bladelets 506-1-$i$ is the obscured face. Likewise, the pressure face of each bladelet 506-2-$i$ in blade 504-2 is the "visible" face and the suction face is the obscured face.

In accordance with the illustrative embodiment, the pressure face of the bladelets is concave and the suction face of the bladelets is convex. In other words, during normal operation, the concave face of the bladelets is the leading face (i.e., the face that is pushing through the fluid).

As previously described, this geometry is analogous to that of a metallic wind-up tape measure. A tape measure can be extended many feet against gravity, yet remain substantially straight if the tape is in a concave-side-up orientation. In this orientation, the concave side of the tape measure is exposed to the load (i.e., gravity). If, however, the tape measure is inverted, so that it assumes a concave-side-down orientation, the tape will readily succumb to gravity and buckle and fold. In this manner, the curvature of the tape measure provides rigidity against buckling/folding when exposed to loads, but only in one direction. Similarly, bladelets 506-1-$i$ and 506-2-$i$ depicted in FIG. 5 provide the same one-way rigidity when exposed to a load, such as the mass of the fluid being pumped. But it is critical that the pressure face is concave.

FIG. 6 depicts additional detail of an individual bladelet, which is representative of bladelets 506-1-$i$ and 506-2-$i$. Other bladelets that would normally be present to collectively define a blade are not depicted in FIG. 6 for the sake of clarity. The bladelet depicted in FIG. 6 is characterized by root 608, tip 610, edge 612 and edge 614. Face 620 is concave and face 622 is convex.

Like bladelets 206-$i$ of impeller 200, the ratio of the chord length of tip 610 to the chord length of root 608 of each concave/convex bladelet is typically in a range from about 1 to about 4, and more typically in a range from about 1.5 to about 3. The ratio of the span of a bladelet to the chord length of tip 610 of a bladelet is typically in a range from about 1 to about 4, and more typically in a range from about 1.5 to about 4. The ratio of the span of a bladelet to the diameter of hub 602 is typically in a range from about 0.5 to about 3, and more typically in a range from about 1 to about 2. The radius of curvature of root 608 is typically in a range of about 0.2 to about 2.5 times the chord length of the root. This equates to curvature for root 608 that is in a range of about 12 degrees to about 150 degrees. More typically, the curvature of root 608 will be within the range of about 30 degrees to about 60 degrees.

Returning to FIG. 5, adjacent bladelets 506-1-$i$ in blade 504-1 overlap near the tips thereof. Likewise, adjacent bladelets 506-2-$i$ in blade 504-2 overlap near the tips thereof. The precise amount of overlap will vary as a function of bladelet geometry; in particular the ratio of the chord length of tip 610 (FIG. 6) to the chord length of root 608, among other parameters. The greater the ratio, the greater the overlap, as a function of the root spacing between adjacent bladelets. In some embodiments, overlap is minimal, such that the trailing edge and leading edge at the tip of adjacent bladelets simply abut each other.

In some embodiments, the concave/convex bladelets disclosed herein are foldable, like bladelets 206-$i$. In such embodiments, FIG. 5 can be considered to depict the bladelets of an impeller in an unfolded or deployed state and FIG. 7 shows bladelets of an impeller in a folded or delivery state.

In some of the embodiments in which the concave/convex bladelets are intended to be foldable, they are formed from a material that is characterized by a resilience or an ability to return to a specific configuration once a restraining force that is deforming the bladelets is withdrawn. Foldable bladelets can suitably be formed from superelastic Nitinol, stainless steel, or various polymers, such as polyimide, polypropylene, and the like.

For initial deployment (e.g., into a patient's vasculature, etc.), foldable concave/convex bladelets can be folded by advancing conduit 728 (e.g., catheter, etc.) over hub 702 and bladelets 706-1-$i$ of blade 706-1 and 706-2-I of blade 706-2. (Most of the bladelets of blade 706-2 are obscured.) When conduit 728 is withdrawn, the bladelets unfold via the potential energy stored in the bladelets during the folding process.

Figure 8A:
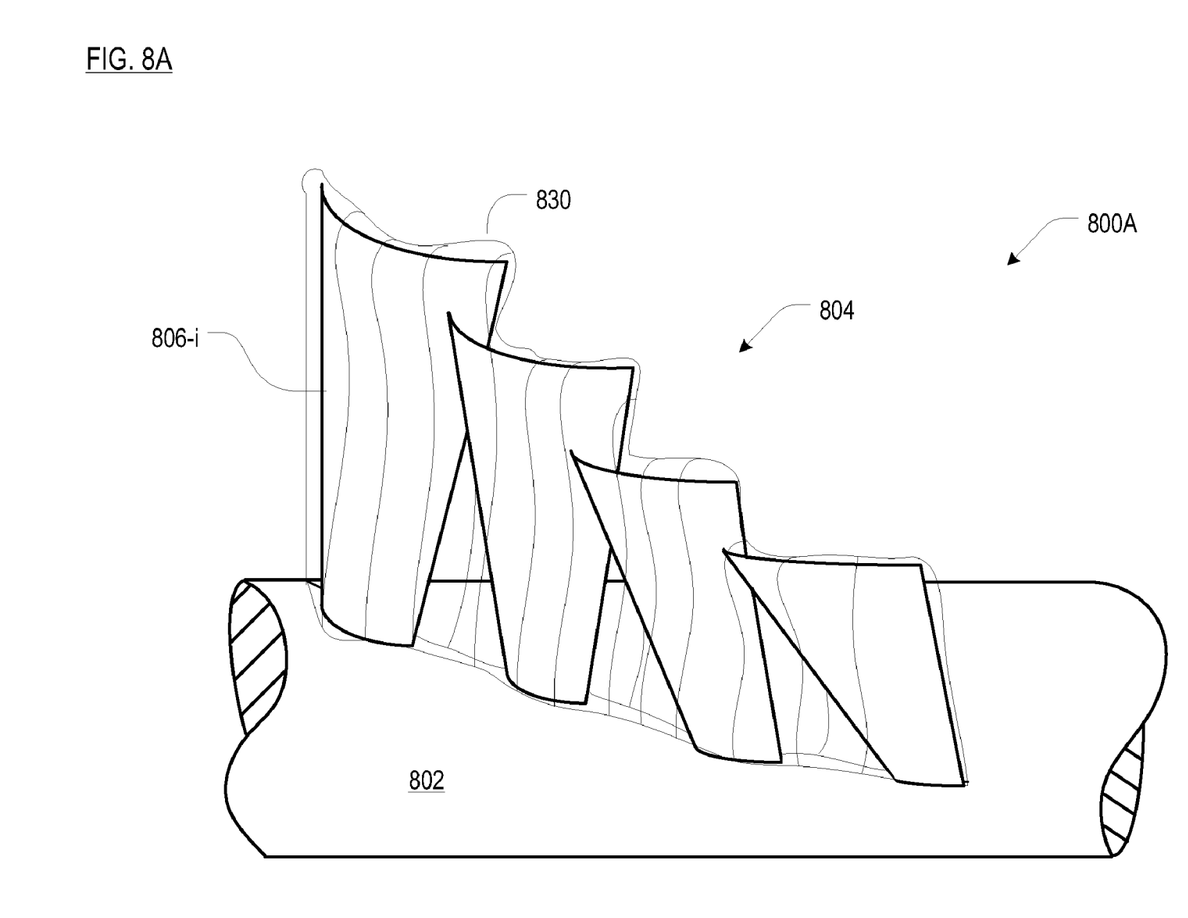
FIG. 8A depicts an embodiment of an impeller in accordance with the present teachings, wherein a blade, which comprises a plurality of bladelets, is covered by a membrane.
Figure 8B:
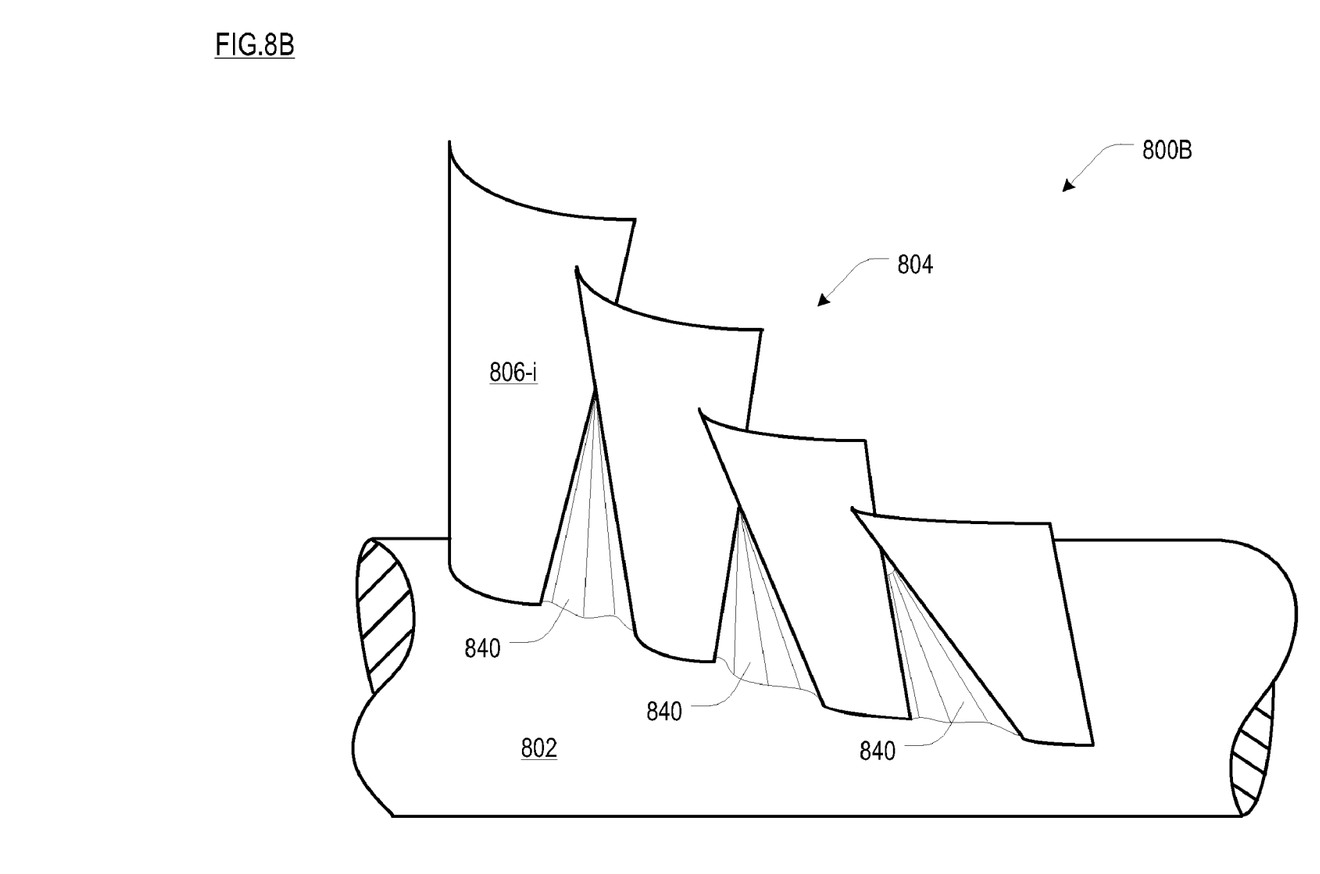
FIG. 8B depicts an embodiment of an impeller in accordance with the present teachings, wherein a membrane connects adjacent bladelets of an impeller blade.

In the various embodiments of impellers disclosed herein, there is some open space between adjacent bladelets beneath the tips thereof. Fluid (e.g., blood, etc.) will pass through this space, thereby resulting in decreased impeller efficiency. To prevent that from happening, in some embodiments, a membrane is disposed over or between the bladelets. FIGS. 8A and 8B depict two embodiments of impellers with membranes.

FIG. 8A depicts impeller 800A having membrane 830 that completely encapsulates blade 804 and all bladelets 806-$i$. The membrane can either be bonded to the root of each bladelet or to hub 802 near the root. FIG. 8B depicts impeller 800B wherein membrane 840 is implemented as a webbing that is disposed between opposing peripheral edges of adjacent bladelets 806-$i$. In other words, in the embodiment depicted in FIG. 8B, membrane 840 covers only a portion of blade 804 whereas for the embodiment depicted in FIG. 8A, membrane 830 covers the full blade.

As a function of application specifics, the membrane may be formed from polyurethane, silicone, latex rubber, other elastomeric compounds, or a biologic membrane such as bovine pericardium.

Figure 9A:
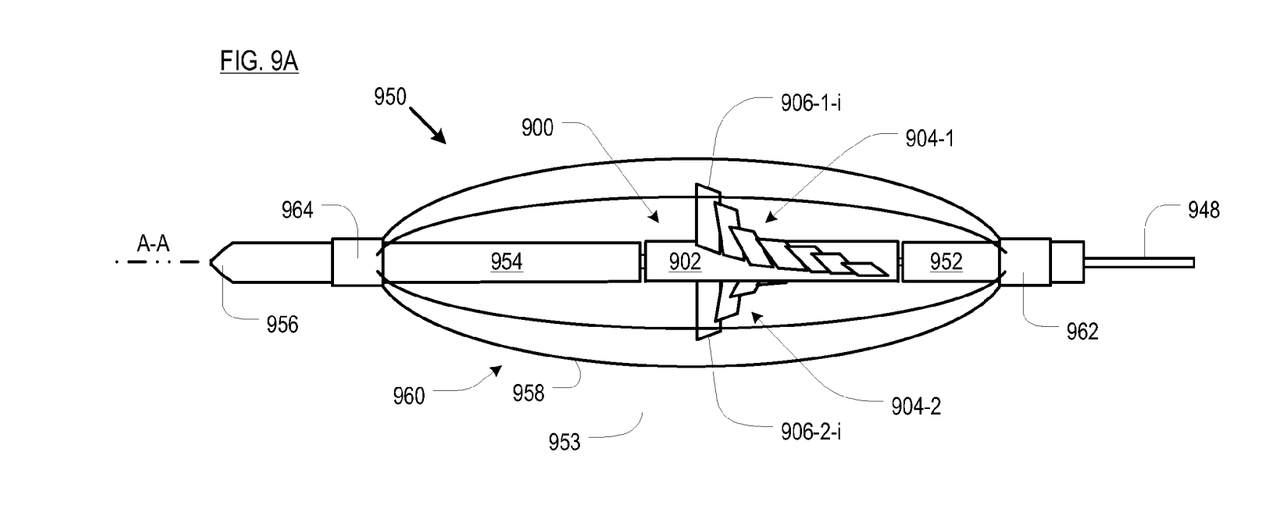
FIG. 9A depicts a blood pump that incorporates an expandable impeller in accordance with the present teachings. The blood pump is shown in an operational state in which the impeller is deployed or unfolded.
Figure 9B:
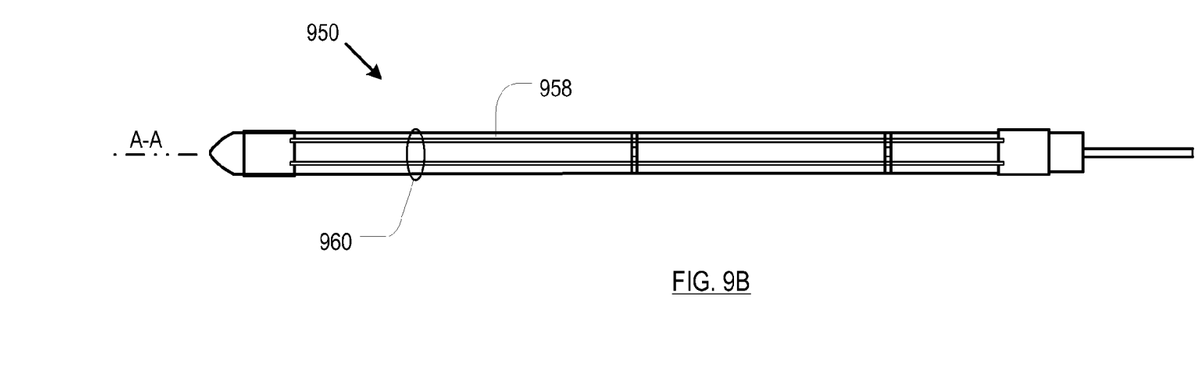
FIG. 9B depicts the blood pump of FIG. 9A, wherein the blood pump is shown in a collapsed or delivery state in which the impeller is folded.

FIGS. 9A and 9B depict the pump-assembly portion 950 of a temporary cardiac assist device or blood pump, as is suitable for percutaneous insertion into the vascular system of a patient.

Since pump assembly 950 is intended for percutaneous insertion, it is advantageously sized so that it can be introduced into the vascular system (e.g., Femoral artery, etc.) via a 12-French or smaller-diameter catheter. Historically, it has been difficult to achieve average flows greater than about 2 to 2.5 liters per minute against physiologic pressures through a 12-French catheter, which has a diameter of 4 millimeters. To that end, pump assembly 950 is collapsed for insertion and delivery, as depicted in FIG. 9B, and expanded for pumping (as depicted in FIG. 9A) when it reaches its intended deployment site.

Pump assembly 950 includes proximal support housing 952, impeller 900, distal support 954, nose cone 956, casing 960, proximal support ring 962, and distal support ring 964.

Pump assembly 950 is based on a design for a percutaneously-inserted, expandable, cardiac-assist device that was disclosed in U.S. Published Pat. Application 2008/0132747, incorporated by reference herein. Pump assembly 950 departs from that design by incorporating an impeller having a plurality of overlapping bladelets as disclosed herein. That document can be referenced for additional information concerning the pump assembly design.

Impeller 900 comprises impeller hub 902 and two impeller blades 904-1 and 904-2 that are arranged in a single blade row. Each impeller blade comprises a plurality of overlapping bladelets 906-1-$i$ and 906-2-$i$.

A plurality of spaced-apart ribs 958 are axisymmetrically arranged about central axis A-A of pump assembly 950. The ribs collectively define cage or casing 960. In the embodiment that is depicted in FIG. 9A, wherein the pump assembly is in the expanded state, the ribs exhibit an arcuate shape, so that open, cage-like casing 960 adopts a typically ellipsoidal or prolate-spheroid form. In this state, the casing exhibits its maximum diameter. This maximum or enlarged diameter is required to accommodate impeller blades 904-1 and 904-2 when they are deployed for operation.

Casing 960 provides one or more of the following functions:
  it prevents the spinning impeller blades of pump assembly 950 from contacting anatomical features;
  it establishes structural integrity;
  it provides a framework for an overlying membrane.

Regarding the final point above, a membrane (not depicted for reasons of clarity) covers a portion of casing 960; the end regions of the casing remain uncovered. The purpose of the membrane is to channel or confine the blood in the vicinity of impeller blades 904-1 and 904-2 so that a flow field develops. Blood enters and exits pump assembly 950 through the uncovered regions of the casing. In various embodiments, the membrane is formed from polyurethane, silicone, latex rubber, or other elastomeric compounds.

In some embodiments, ribs 958 are formed in such a way (e.g., processing, materials of fabrication, etc.) that in the absence of a restraining force, they exhibit the aforementioned non-planar (e.g., arcuate, etc.) shape, such that pump assembly 950 "naturally" assumes the expanded configuration. As a consequence, no actuating force is required to place pump assembly 950 into its operating configuration. Rather, for such embodiments, a force must be applied to restrain pump assembly 950 from expanding. A super-elastic material such as nitinol, etc., can be used to form ribs 952.

Elements of pump assembly 950 are coaxial and, in some cases, linearly arranged with respect to one another. This provides stability to pump assembly 950. Specifically, in the illustrative embodiment, proximal support housing 952, impeller hub 902, and distal support 954 are linearly arranged. Proximal support housing 952 and impeller hub 902 are coaxial with respect to drive shaft 948. Casing 960, which comprises ribs 958, proximal support ring 962, and distal support ring 964, is coaxial with respect to proximal support housing 952, impeller hub 902, and distal support 954. In some embodiments, proximal support housing 952, impeller hub 902, and distal support 954 comprise injection molded polymer.

To develop pumping action, torque from an extracorporeal motor (not depicted) must be delivered to impeller blades 904-1 and 904-2. This is accomplished via a flexible drive cable (not shown) and rigid drive shaft 948.

In more detail, the proximal end of the drive cable is coupled to the motor and the distal end of the drive cable is coupled to drive shaft 948. The drive shaft enters the proximal end of pump assembly 950 and is operatively coupled to impeller hub 902. The drive shaft extends a relatively short distance (less than about 3 centimeters) proximal of pump assembly 950.

The drive cable and the drive shaft are distinct components and the distinction between them is an important one. In particular, the drive cable must be flexible to enable it to be easily advanced in the vasculature and, if required, beyond the aortic arch. In contrast, drive shaft 948 is rigid in order that the requisite seal and bearing in proximal support housing 952 function properly. Although less preferable, it is possible to operate a pump using only a drive cable (i.e., without a drive shaft), with appropriate modifications to the pump assembly and/or drive cable.

In the illustrative embodiment, drive shaft 948 passes through proximal support housing 952 to impeller hub 902 and terminates therein. In some embodiments, the drive shaft terminates approximately at the axial mid-point of impeller hub 902. Proximal support housing 952 provides a non-rotating support surface for the proximal support ring 962, thereby supporting the proximal end of casing 960. Since casing 960 does not rotate, it cannot couple to a rotating surface, such as impeller hub 902.

Since proximal support housing 952 does not rotate but impeller hub 902 does, they are separated by gap. And since drive shaft 948 passes through proximal support housing 952, a bearing must be provided within the housing to accommodate the rotational movement of drive shaft 948. A seal must also be provided within proximal support housing 952 to prevent blood from entering. If blood were to enter housing 952 in the small gap between drive shaft 948 and the bore that accepts it, the blood might be hemolyzed by the action of drive shaft 948.

The bore of the bearing within proximal support housing 952 provides substantially all of the structural rigidity for impeller blades 904-1 and 904-2/impeller hub 902. Materials suitable for the bearing include, without limitation, low friction polymers, such as Teflon® (polytetrafluoroethylene), Torlon® (polyamide-imide), Rulon® (propriety polytetrafluoroethylene-based compounds), Vespel® (thermoplastic polyimide) sleeve bearings, biocompatible bearings and the like. In some embodiments, polyurethane or silicon lip seals or o-rings are used as the seal.

In some embodiments, drive shaft 948 is formed as an integral part of impeller hub 902. In some other embodiments, impeller hub 902 is formed around drive shaft 948. In any case, drive shaft 948 is rigidly coupled to impeller hub 902 to efficiently drive the impeller blades. Drive shaft 948 is formed of stainless steel or other materials having specific dimensions, hardness, surface finish, and radiused edges for damage-free seal insertion. Surface finish will be specified by the bearing or seal manufacturer to ensure compatibility with same.

In some embodiments, the drive cable (not shown) is formed of stainless steel (but in such a way that the cable remains flexible). In some embodiments, the drive cables disclosed in U.S. patent application Ser. No. 11/758,402 are used.

Impeller blades 904-1 and 904-2 are depicted in a deployed or unfolded state in FIG. 9A. In this state, they extend substantially orthogonally from impeller hub 902.

The impeller blades comprise a plurality of bladelets, consistent with embodiments described earlier in this disclosure. In preferred embodiments, the bladelets have concave pressure side and a convex suction side, as per impeller 500 of FIG. 5. In the illustrative embodiment, the bladelets of impeller blades 904-1 and 904-2 are biased to deploy; that is, they must be restrained to be kept in the folded state. In that embodiment, the bladelets are formed of a resilient material, as previously described. In some other embodiments, the bladelets must be "spun-up" to the deployed state. In other words, the rotation of the impeller hub causes the bladelets to deploy. In a collapsed state, impeller 900 has a diameter of about 3 millimeters (9 Fr).

For the illustrative embodiment, the design speed of the impeller is in the range of between about 1,000 RPM to about 20,000 RPM. The impeller is expected to pump at least 2.5 liters per minute of blood at 100 mmHg (4 cP) and 37° C. using a 10 Fr delivery system. The impeller is designed for a 100% duty cycle for a seven-day service life.

The following dimensions provide an impeller design suitable for use in conjunction with pump assembly 950 for the design conditions stated above. It is to be understood that the dimensions are provided as indicative of a typical design for impellers described herein, when used in this service:

Diameter of impeller hub 902: about 2 millimeters (mm)
Span of impeller bladelets 906-1-i/906-2-i: about 3 mm
Chord length of bladelets at the root: about 1 mm
Chord length of bladelets at the tip: about 2 mm
Bladelets per blade 904-1/904-2: typically 3-7
Radius of curvature of bladelets at root: about 1 mm
Radius of curvature of bladelets at tip: greater than 2 mm Casing 960 is advantageously supported at its distal end. Such support is provided by distal support 954, which receives distal support ring 964. Like proximal support housing 952, the distal support is not rotating. Since, however, impeller hub 902 is rotating, the impeller hub and distal support 954 are separated by a gap. Because drive shaft 948 does not extend beyond the impeller blades, a locating pin or other means is required to couple distal support 954 to impeller hub 902.

In the illustrative embodiment, locating pin 953 depends from proximal end of distal support 954. The pin couples the proximal end of the distal support to the distal end of impeller hub 902. Disposed within the distal end of impeller hub 902 are a bearing and seal (not depicted). Since, as previously disclosed, impeller hub 902 is rotating and distal support 954 is not, a bearing is required to accommodate the differential movement. And the seal prevents leakage of blood into impeller hub 902. In some embodiments, the bearing and seal in the impeller hub are formed of the same materials as the bearing and seal in proximal support housing 952.

The distal end of distal support 954 terminates in nose cone 956, which provides an atraumatic surface that is contoured for easy insertion and navigation through a patient's vascular system.

FIG. 9B depicts pump assembly 950 in its delivery state. In this state, casing 960 (and pump assembly 950) exhibits its minimum diameter. In this state, ribs 952 are straight and substantially parallel to axis A-A of pump assembly 950. Casing 960 adopts a substantially cylindrical shape.

It will be appreciated that to the extent pump assembly 950 has a relatively smaller diameter, the task of negotiating the vascular system, and in particular the aortic arch, is simplified. As a consequence, pump assembly 950 is introduced into the body (e.g., the femoral artery, etc.) in the folded or delivery state. Typically, it is after pump assembly 950 has passed the aortic arch and entered the ascending aorta or other final locations that casing 960 is expanded for operation.

In some embodiments, pump assembly 950 is deployed into the vascular system via an "introducing" tube, such as a catheter, sheath, or the like. In some embodiments, the wall of the introducing tube provides the restraining force to maintain casing 960 in the contracted state. To expand casing 960, pump assembly 950 is simply advanced beyond the distal end of the tube. To provide this functionality, the introducing tube must possess a suitably radially-inelastic wall. Standard catheters are suitably radially-inelastic for this purpose. In conjunction with the present disclosure, it is within the capabilities of those skilled in the art to provide an introducing tube having a suitably radially-inelastic wall to maintain casing 960 in the contracted state.

One of either the proximal end or the distal end of casing 960 is movable in an axial direction. This facilitates the expansion and contraction of the casing. In embodiments in which casing 960 is to be collapsed simply by the act of inserting the proximal end of pump assembly 950 into an introduction/extraction catheter, then it is advantageous (but not necessary) for the distal end of casing 960 to be the movable end. In such embodiments, distal support ring 964 is movably coupled to distal support 964 so that it is able to readily slide along the support in either direction.

Pump assembly 950 may be collapsed as follows for extraction from the vascular system. Optionally, impeller 900 is rotated slowly in the reverse direction, such that the convex face of the bladelets becomes the pressure face. By virtue of their structure, the bladelets will readily collapse once the convex side is exposed to a load. Pump assembly is then drawn back into the introducing tube.

Depending upon materials selection and bladelet geometry, the bladelets might or might not remain collapsed (after the cessation of reverse impeller rotation). For some embodiments in which the bladelets do not remain collapsed, the pump assembly is drawn back into the introducing tube while the impeller is still in motion. The reverse rotational motion is stopped only after the pump assembly is within the introducing tube, wherein the wall of the tube will maintain the bladelets in the collapsed state.

Alternatively, impeller rotation is simply stopped and pump assembly 950 is drawn back into the introducing tube. One benefit of the curved structure of the bladelets is that, even though the "closure" force is being applied to the side that is best able to resist it, once the buckling force is exceeded, the bladelets will readily fold and collapse against hub 902.

It is to be understood that the above-described embodiments are merely illustrative of the present invention and that many variations of the above-described embodiments can be devised by those skilled in the art without departing from the scope of the invention. For example, in this Specification, numerous specific details are provided in order to provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the Specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

What is claimed:

1. An apparatus comprising an impeller, wherein the impeller comprises:
 a hub; and
 a first plurality of bladelets disposed on the hub, wherein the first plurality of bladelets collectively define a first blade, wherein each bladelet has a root, a tip, a pressure face and a suction face, and further wherein:
 (a) each bladelet is movable between a deployed state in which the tip thereof is relatively further from the hub and a non-deployed state in which the tip is relatively closer to the hub;
 (b) the pressure face of each bladelet is concave; and
 (c) the root of each bladelet is narrower than the tip of each bladelet.

2. The impeller of claim 1 further comprising a second plurality of bladelets disposed on the hub, wherein the second plurality of bladelets collectively define a second blade, and wherein the first plurality of bladelets and the second plurality of bladelets are diametrically opposed about the hub, the first and second blade collectively defining a first blade row.

3. The impeller of claim 1 wherein the first plurality of bladelets are helically arranged about the hub.

4. The impeller of claim 1 wherein the suction face of each bladelet is convex.

5. The impeller of claim 1 wherein a ratio of chord length of the tip to the chord length of the root is at least about 1.5.

6. The impeller of claim 1 wherein a ratio of a span of each bladelet to a chord length of the tip of each bladelet is at least about two.

7. The impeller of claim 1 wherein respective tips of adjacent bladelets abut each other.

8. The impeller of claim 1 wherein leading and trailing peripheral edges of each bladelet are straight.

9. The impeller of claim 1 further comprising a membrane, wherein the membrane covers at least a portion of the first blade.

10. The apparatus of claim 1 further comprising:
 a flexible drive cable; and
 a rigid drive shaft, wherein the flexible drive cable and the rigid drive shaft are coupled to one another, and further wherein the hub is operatively coupled to the drive shaft.

11. The apparatus of claim 10 further comprising an extracorporeal motor, wherein the motor is coupled to the flexible drive cable.

12. An apparatus comprising an impeller, wherein the impeller comprises:
 a hub;
 a first blade depending from the hub; and
 a second blade depending from the hub and diametrically opposed to the first blade, wherein the impeller is a single-stage impeller having a single blade row, and further wherein:
 (a) the blade row comprises the first blade and the second blade;
 (b) the first blade and the second blade are segmented into bladelets, each bladelet having a root, a tip, and a pressure face;
 (c) the bladelets are widest at the tip thereof and narrowest at the root;
 (d) each bladelet is foldable proximate to the root thereof; and
 (e) the pressure face of each bladelet is concave.

13. The impeller of claim 12 wherein the bladelets that define the first blade are helically arranged about the hub.

14. The impeller of claim 12 wherein respective roots of adjacent bladelets are spaced apart from one another.

15. The impeller of claim 12 wherein respective tips of adjacent bladelets overlap.

16. The impeller of claim 12 wherein respective tips of adjacent bladelets abut each other.

17. The impeller of claim 12 further comprising a first membrane and a second membrane, wherein the first membrane covers at least a portion of the first blade and the second membrane covers at least a portion of the second blade.

18. The apparatus of claim 12 further comprising:
 a flexible drive cable; and
 a rigid drive shaft, wherein the flexible drive cable and the rigid drive shaft are coupled to one another, and further wherein the hub is operatively coupled to the drive shaft.

19. The apparatus of claim 18 further comprising an extracorporeal motor, wherein the motor is coupled to the flexible drive cable.

20. An apparatus comprising an impeller, wherein the impeller comprises:
 a hub; and
 a first plurality of bladelets disposed on the hub, wherein the first plurality of bladelets collectively define a first blade, wherein each bladelet has a root and a tip, and further wherein each bladelet is movable between a deployed state in which the tip thereof is relatively further from the hub and a non-deployed state in which the tip is relatively closer to the hub.

21. The impeller of claim 20 wherein at least some of the bladelets are widest at the tip and narrowest at the root thereof.

22. The impeller of claim 20 wherein each bladelet has a pressure face and a suction face, and further wherein the pressure face of at least some of the bladelets is concave.

23. The impeller of claim 20 wherein each bladelet has a pressure face and a suction face, and further wherein the suction face of at least some of the bladelets is convex.

24. The impeller of claim 20 wherein the first plurality of bladelets are helically arranged about the hub.

25. The impeller of claim 20 wherein a membrane covers at least a portion of the first blade.

26. The impeller of claim 20 further comprising a second plurality of bladelets disposed on the hub, wherein the second plurality of bladelets collectively define a second blade, wherein the first and second blade collectively define a first blade row, and wherein the first blade row exhibits n-fold symmetry, wherein n is the number of blades in the first blade row.

27. The impeller of claim 20 wherein the tip of adjacent bladelets abut each other.

28. The impeller of claim 20 wherein the tip of adjacent bladelets overlap each other.

29. The apparatus of claim 20 further comprising:
 a flexible drive cable; and
 a rigid drive shaft, wherein the flexible drive cable and the rigid drive shaft are coupled to one another, and further wherein the hub is operatively coupled to the drive shaft.

30. The apparatus of claim 29 further comprising an extracorporeal motor, wherein the motor is coupled to the flexible drive cable.

* * * * *